United States Patent [19]

McCormick

[11] 4,146,364

[45] Mar. 27, 1979

[54] MIXING APPARATUS AND METHOD FOR BLOOD CELL SUSPENSIONS

[76] Inventor: James B. McCormick, 505 N. Lakeshore Dr., Chicago, Ill. 60611

[21] Appl. No.: 905,183

[22] Filed: May 12, 1978

[51] Int. Cl.[2] .................... G01N 33/16; B01F 11/00

[52] U.S. Cl. .................... 23/230 B; 23/230 A; 366/209; 366/239; 422/105; 422/116

[58] Field of Search .................... 23/259, 230 B, 230 A, 23/292, 253 R; 366/239, 211, 209; 356/39; 324/71 R, 71 CP

[56] References Cited

U.S. PATENT DOCUMENTS

| | | | |
|---|---|---|---|
| 3,463,614 | 8/1969 | Leslie | 23/253 X |
| 3,488,156 | 1/1970 | Good et al. | 23/253 R |
| 3,617,222 | 11/1971 | Matte | 23/230 R |
| 3,876,379 | 4/1975 | Ghim | 23/259 |

*Primary Examiner*—R.E. Serwin
*Attorney, Agent, or Firm*—Fitch, Even, Tabin & Luedeka

[57] ABSTRACT

A mixing apparatus particularly adapted for mixing blood cell suspensions and which includes a support platform having discrete troughs adapted to receive a plurality of specimen container tubes and effect rocking of the tubes to uniformly mix blood cell suspensions without distorting, breaking or foaming the suspensions. The platform may be randomly loaded with specimen tubes and is adapted to effect rocking of the platform in response to the presence of a tube within a trough, and provides first signals indicating the presence of tubes within the individual troughs and second signals indicating lapse of a predetermined mixing time for each specimen tube.

13 Claims, 6 Drawing Figures

MIXING APPARATUS AND METHOD FOR BLOOD CELL SUSPENSIONS

The present invention relates generally to mixing apparatus, and more particularly to a novel mixing apparatus particularly adapted for uniformly mixing blood cell suspensions for predetermined periods of time without distorting, breaking or foaming the suspensions.

In the laboratory analysis of fluid specimens, such as blood specimens, it is desirable that the specimens be thoroughly and uniformly mixed to provide homogeneous samples on which laboratory tests are carried out. This is particularly desirable where test specimens are graded against a set of standard specimens, in which case uniform mixing and homogeneity of the different sample specimens is necessary to assure that a true comparative analysis may be obtained. In practice, blood specimens are randomly delivered in tubular containers, such as test tubes, to the count testing station so that variations in the sedimentation which separates cells and plasma by gravity may occur. If a tube is subsequently mixed manually by shaking the tube, non-standard mixing is achieved between the specimen tubes with the result that wide variances are obtained in the test end points. If the specimen tubes are mechanically mixed or rotated, such as on a rocking support table, the specimens have an opportunity to be mechanically mixed but there is no random control of time nor other indication of completion of a predetermined period of mixing for each sample specimen. There thus exists a need for apparatus capable of uniformly mixing random blood cell suspensions for predetermined mixing periods without distorting, breaking or foaming the blood cell suspensions.

One of the primary objects of the present invention is to provide novel mixing apparatus which provides uniform and timed mixing of radom liquid suspensions without distorting, breaking or foaming the suspensions.

A more particular object of the present invention is to provide a mixing apparatus particularly adapted for mixing blood cell suspensions in specimen containers, which apparatus provides means for detecting the presence of discrete specimen containers on the apparatus and effecting uniform mixing of the discrete suspensions for timed periods after which indicator means signal that mixing is complete.

A feature of the mixing apparatus of the present invention lies in the provision of a rockable support platform having a plurality of parallel troughs thereon each of which is adapted to receive a fluid specimen container tube, the apparatus having a control circuit which includes means associated with each trough to detect the presence of a fluid specimen tube therein and trigger a timing circuit operative to time out a predetermined mixing period after which a signal is provided to indicate completed mixing for the corresponding specimen tube.

Further objects and advantages of the present invention, together with the organization and manner of operation thereof, will become apparent from the following detailed description of the invention when taken in conjunction with the accompanying drawings wherein like reference numerals designate like elements throughout the several views, and wherein.

Figure 1:
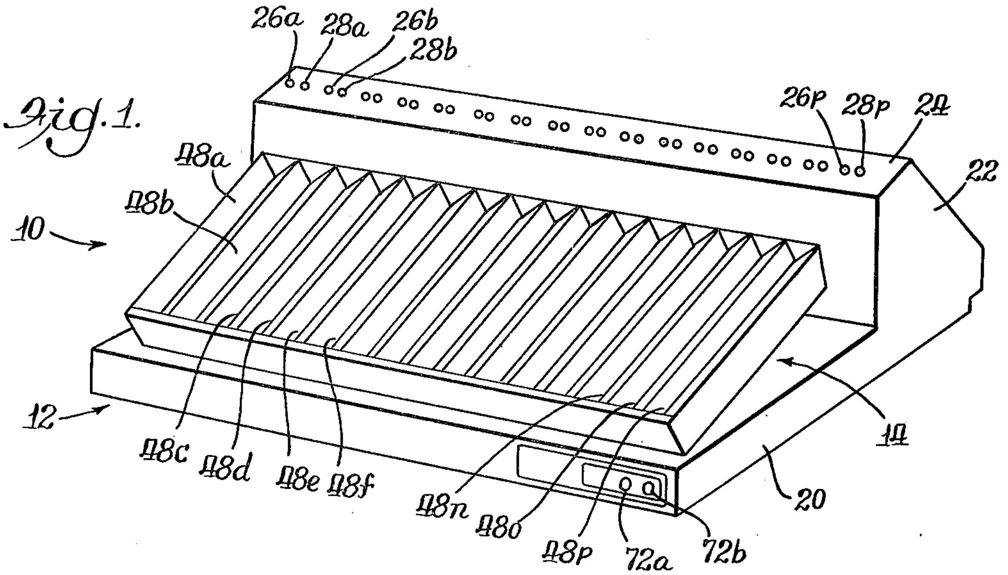
FIG. 1 is a perspective view of a mixing apparatus constructed in accordance with the present invention.

Referring now to the drawings, and in particular FIG. 1, a mixing apparatus constructed in accordance with the present invention is indicated generally at 10. The mixing apparatus, which alternatively may be termed a blood sample mixer, is particularly adapted for effecting gentle uniform mixing of blood cell suspensions which are contained within fluid sample containers taking the form of conventional test tubes open on one end and adapted to be closed by conventional plug or cap closures so as to provide liquid tight containers. Very generally, the mixing apparatus 10 includes base means 12 on which is mounted specimen tube support means 14 for cyclical rocking movement about a pivot axis extending longitudinally of the apparatus. The mixing apparatus includes drive means, indicated generally at 16 in FIG. 3, operatively associated with the specimen tube support means 14 and adapted to effect gentle rocking movement thereof about its pivot axis. The mixing apparatus further includes a control circuit, to be described in greater detail hereinbelow, operatively associated with the drive means 16 and the rockable tube support means 14 and operative to effect rocking of the tube support means in response to the presence of a specimen tube on the tube support means and also provide first signals indicating the presence of individual specimen tubes on the support means and second signals indicating lapse of a predetermined mixing time for each specimen tube.

The base means 12 includes a structural base or housing which may be made of suitable sheet metal to define a substantially rectangular base portion 20 terminating at its rearward edge in an upstanding portion 22 which serves to house various operating components of the mixing apparatus. The upstanding portion 22 has a forwardly and downwardly inclined upper wall 24 in which is mounted a plurality of indicating elements **26*a*, *b*, *c* etc., and 28*a*, *b*, *c*** etc., the purpose of which will become apparent below.

To facilitate pivotal or rocking support of the specimen tube support means 14, the rectangular base portion 20 is provided with a generally centrally located raised portion 32 which extends longitudinally of the base means 12 and supports on its upper surface 34 a pivot shaft 36 through a pair of longitudinally spaced mounting blocks **38*a* and 38*b*. In the illustrated embodiment, the specimen tube support means 14 takes the form of a specimen tube support platform 40 having a tubular sleeve 42 secured to its lower surface 44** so as to extend along the longitudinal center axis of the surface 44. The support sleeve 42 has a pair of transverse slots, one of which is shown at 46 in FIG. 2, formed therein to facilitate mounting of the sleeve 42 on the pivot shaft 36 and thereby define the pivot or rocking axis of the support platform 40.

Figure 2:
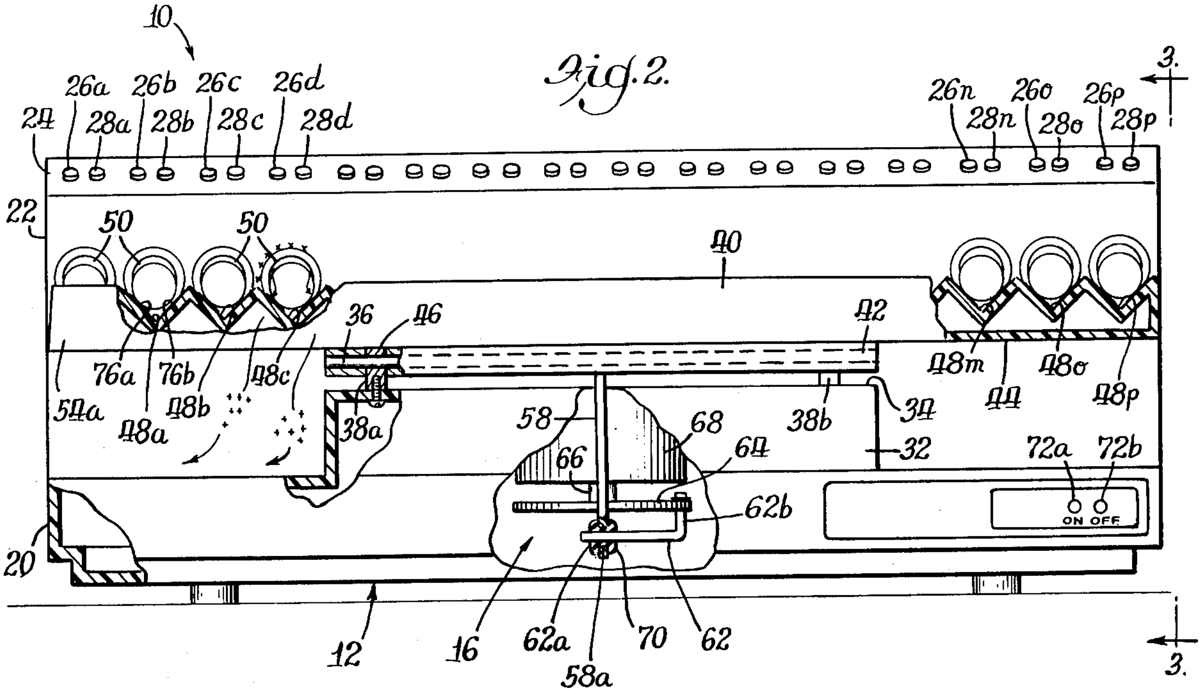
FIG. 2 is a front elevational view, on an enlarged scale, of the mixing apparatus of FIG. 1, the rocking platform being shown in a substantially horizontal position and with portions of the apparatus broken away for clarity.
Figure 3:
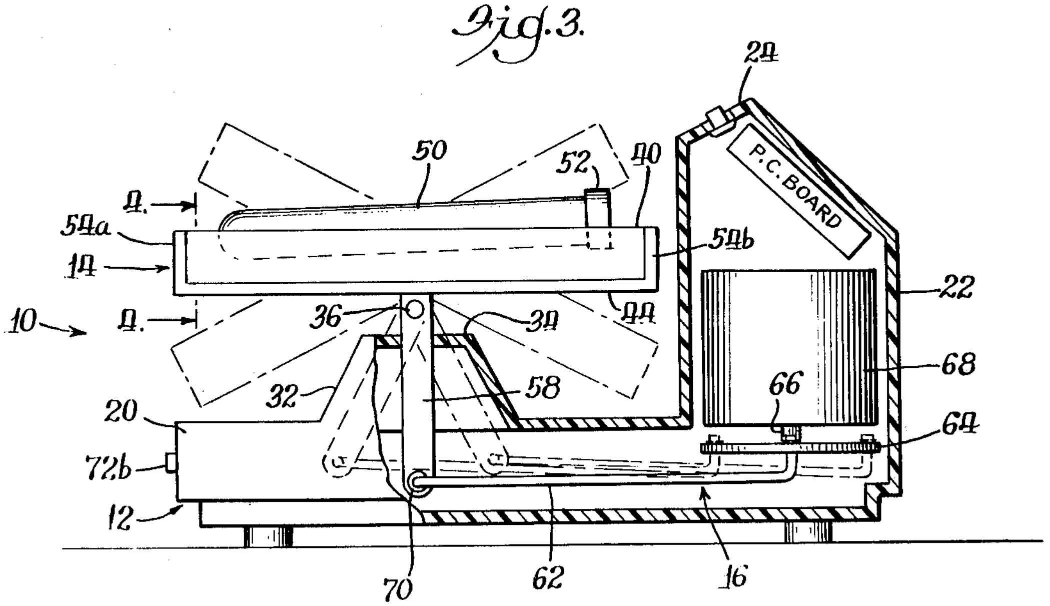
FIG. 3 is an end view taken substantially along line 3—3 of FIG. 1, portions being broken away for clarity and with the rocking platform being shown in its extreme rocking positions in phantom.
Figure 4:
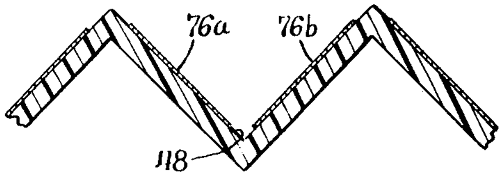
FIG. 4 is a fragmentary sectional view, on an enlarged scale, taken substantially along line 4—4 of FIG. 3 and illustrating a specimen tube trough of the rocking platform.

The support platform 40 is made of a dielectric material, such as molded plastic, and defines a plurality of discrete substantially parallel sample tube receiving troughs 48*a, b, c* etc., each of which is adapted to receive a specimen container tube, such as indicated at 50 in FIG. 2, in supporting relation therewith such that the longitudinal axes of the specimen tubes lie in planes normal and transverse to the pivot shaft 36. The specimen container tubes 50 preferably comprise conventional test tubes each of which has a closed rounded end 50*a* (FIG. 3) and an open opposite end 50*b* adapted to receive a plug or closure cap 52 therein to effect liquid-tight sealing of the container tube. In the illustrated embodiment, the specimen tube receiving troughs 48*a, b, c* etc., of which there are 16 in the described embodiment, are V-shaped in transverse cross section with the apex of the V-shape being disposed to lie in a common vertical plane with the longitudinal axis of a sample tube 50 when placed therein, as best seen in FIG. 4. The support platform 40 has upwardly extending forward and rear walls 54*a* and 54*b* which serve to retain specimen tubes 50 longitudinally within the troughs 48. With a plurality of the specimen tubes 50 supported within discrete support troughs 48*a, b, c,* etc., of the support platform 40, rocking movement of the platform about its pivot axis 36 will effect mixing of the fluid contents within the sample tubes.

To effect the desired cyclical rocking movement of the specimen tube support platform 40 about its pivot axis 36, the support platform has a lever arm 58 secured to its lower surface 44 at substantially its geometrical center. The lever arm 58 is disposed in normal relation to the plane of the lower surface 44 and extends downwardly through a suitable opening 60 in the raised base portion 32, as best seen in FIG. 3. The lower end of the lever arm 58 is pivotally connected to an end 62*a* of a crank shaft or connecting linkage 62 which has its opposite end 62*b* connected eccentrically to a circular drive plate or disc 64 mounted coaxially on the drive shaft 66 of a constant speed electric drive motor 68. The drive motor 68 preferably comprises a relatively low constant speed motor, such as 30–60 rpm, to effect relatively slow gentle rocking motion of the tube support platform. The end 52*a* of the drive linkage 62 interfits with a suitable opening 58*a* in the lever arm 58 through a resilient grommet 70 to allow articulation of the drive linkage 66 during rotation of the drive plate 64. The drive motor 68, drive plate 64 and associated drive linkage 62 comprise the drive means 16 for the specimen tube support platform 40 and are operative when the motor 68 is energized to effect cyclical rocking of the tube support platform about its pivot axis 36.

The configuration of the rectangular base 20 of the apparatus, the tube support platform 40 and the lever arm 58 are such that the tube support platform 40 undergoes a total angular pivotal movement of approximately 60 degrees between its extreme rocking positions, as shown in phantom in FIG. 3, for each revolution of the drive plate 64. The motor 68 is connected to a suitable electric power supply and may be energized through selective actuation of "on" and "off" switches 72*a* and 72*b*, respectively, mounted on the forward edge of the base means 12, as best seen in FIG. 2. During operation of the mixing apparatus 10, the drive motor 68 is continually energized so as to maintain the specimen tube support platform 40 in continual rocking motion.

In accordance with an important feature of the present invention, the mixing apparatus 10 includes a control circuit adapted to detect the presence of a specimen tube 50 placed within any of the tube receiving troughs 48*a, b, c,* etc., and initiate a timing circuit for each specimen tube simultaneously with providing a visual indication for each trough that a specimen tube placed therein is undergoing mixing. After expiration of a predetermined mixing period for each specimen tube placed on the support platform, the signal which had been initiated to indicate that a particular tube is undergoing mixing is terminated, and a second signal is provided indicating that mixing for that particular specimen tube is complete and the tube is ready for removal from the apparatus 10. These signals are represented by the aforenoted indicating elements 26*a, b, c,* etc., and 28*a, b, c,* etc., to be described hereinafter.

To detect the presence of a specimen container tube 50 within a tube support trough 48*a, b, c,* etc., in the support platform 40, each V-shaped trough formed in the dielectric support platform has its opposing angularly inclined walls coated with a metallic copper or other appropriate capacitance collector surface as indicated at 76*a* and 76*b* in FIG. 4. The capacitance collector surfaces 76*a* and 76*b* are represented schematically in the schematic circuit diagram of FIG. 5 with a specimen tube 50 shown in phantom received within the corresponding trough so as to engage the surfaces 76*a, b.* The troughs 48*a, b, c,* etc., may take alternative transverse configurations such as U-shaped troughs, although V-shaped troughs are believed to be more economical and provide suitable sensitivity to the presence of a specimen tube therein as will become more apparent hereinbelow.

Figure 5:
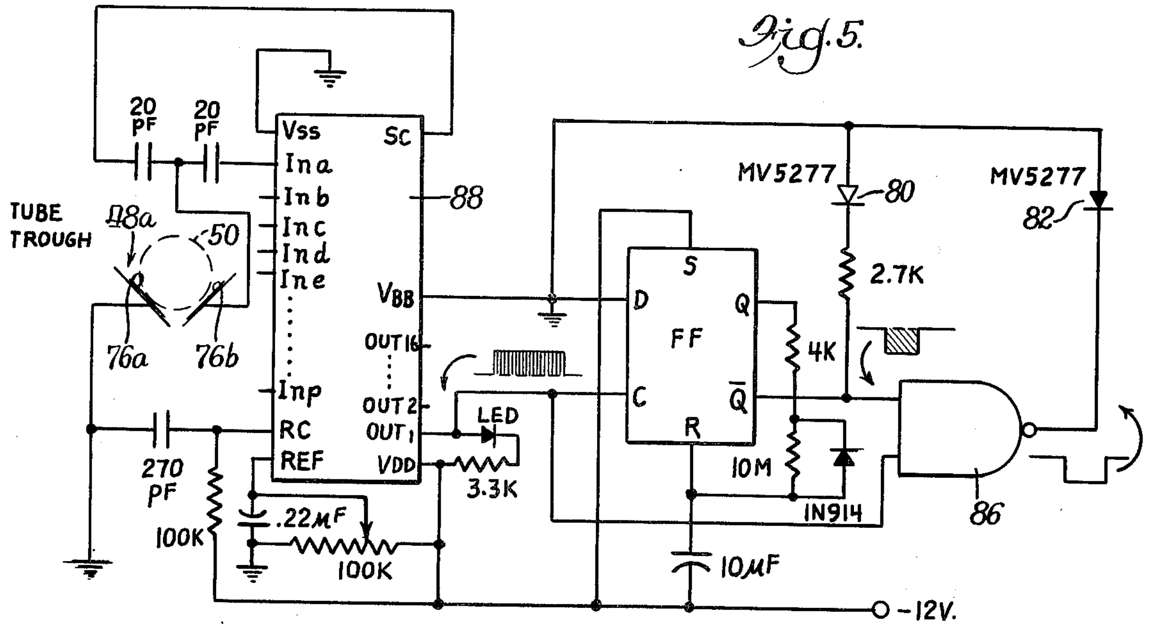
FIG. 5 is a schematic circuit diagram illustrating one channel of a timer-indicator circuit for the mixing apparatus of FIG. 1.
Figure 6:
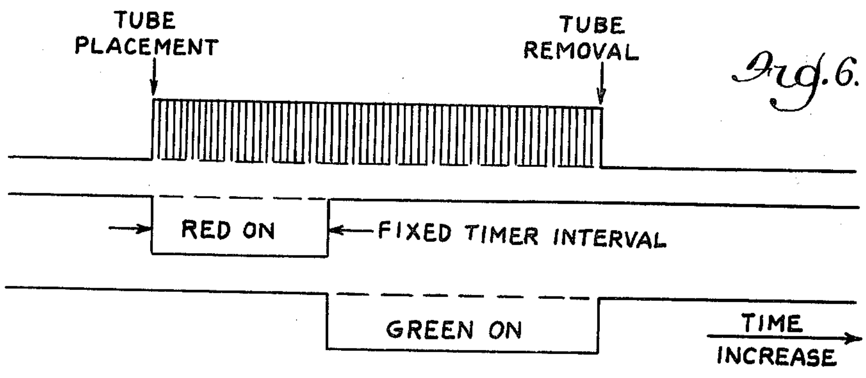
FIG. 6 is a schematic diagram graphically illustrating the timing relationship of the various conditions for one specimen tube channel of the apparatus of FIG. 1.

FIG. 5 schematically illustrates a control circuit for one channel of a multichannel circuit wherein each channel is associated with one of the tube receiving troughs, such as 48*a,* in the illustrated multiple trough support platform 40. The control circuit of FIG. 5, drives a pair of light emitting diodes 80 and 82 which represent the indicating signal elements 26*a* and 28*a,* respectively, mounted on the upper wall 24 of the mixing apparatus. In the illustrated circuit, the light emitting diode (LED) 80 establishes a readily visible red light when a specimen tube 50 is placed within the corresponding trough 48*a* and indicates the presence of a specimen tube within trough 48*a* and also that "time is on", i.e., that the specimen within the specimen tube is undergoing mixing. The LED 82 preferably emits a green light at 28*a* and is energized after a predetermined period of time has expired following placement of a tube within the trough 48*a,* such as 45–60 seconds for a 10 ml blood sample. The green light 82 thus indicates that mixing of the contents of specimen tube 50 in trough 48*a* is complete and that removal of the test tube from the rocking support platform is appropriate. The control circuit is operative to turn the red LED 80 off after the predetermined mixing time has expired and energize the green LED 82 and to keep the green LED 82 energized until the test tube is removed. The LED's 80 and 82 preferably comprise miniature wide-angle low-profile solid state lamps.

The LED's 80 and 82 are driven by a conventional D-type flip-flop 84, which serves as a timer, and a conventional NAND gate 86. The capacitance collector surfaces 76*a*, *b* on each of the 16 tube receiving troughs 48*a*, *b*, *c*, etc., are connected to associated inputs (indicated at $In_a$, $In_b$, $In_c$, etc.) on a scanning capacitance detector 88. The detector is operative to continually scan each trough for the presence of a container tube 50 at a scan time determined by a timing circuit including a potentiometer and a capacitor. When a blood sample containing tube is placed within a selected one of the tube receiving troughs 48*a*, *b*, *c*, etc., the surface and/or content capacitance of the blood sample increases the capacitance across the associated capacitance collector surfaces 76*a*, *b*. This change in capacitance causes a switch means within the detector to close, causing the output associated with the input to go high. The output going high triggers a conventional D-type flip-flop 84 which serves as a timer, the timing of which is determined by a resistance and capacitance circuit connected across the Q output and connected to the reset input. Triggering of the flip-flop causes the $\overline{Q}$ output to go low thereby energizing the red LED 80, which is connected thereto, to indicate the presence of a tube within the corresponding tube receiving trough.

After the predetermined minimum time period which, as aforementioned, may be set at approximately 45–60 seconds for a 10 ml blood sample, the $\overline{Q}$ output of the flip-flop becomes low thereby deenergizing the red LED 80. The combination of the high Q output and the high output of the detector energizes the green LED 82 through a NAND gate to thereby indicate that the predetermined mixing period has expired and that the corresponding blood sample container tube is ready for removal from the support platform. The green LED remains energized as long as the container tube remains on the support platform because the output of the detector remains high until the tube is removed. As indicated, the red and green LED's 80 and 82 represent the light signals 26*a* and 28*a* mounted on the wall 24 of the mixing apparatus adjacent the trough 48*a* so as to provide a visual indication to the operator of the mode of mixing, i.e., incomplete or complete, for the associated blood sample tube.

The relationship of the various operating conditions for a blood sample undergoing mixing on the apparatus 10 is illustrated graphically in FIG. 5. It is seen that when a tube is placed on a selected one of the troughs 48*a*, *b*, *c*, etc., the red LED 80 is energized to indicate the presence of a tube on the corresponding trough and the beginning of a predetermined minimum time interval for mixing. After the predetermined mixing period has expired, the red indicator 80 is deenergized and the green indicator element 82 is energized. Energizing the LED 82 provides a visual indication of completion of predetermined minimum mixing and signals readiness for removal of the blood sample container tube from the mixing apparatus.

Thus, in accordance with the present invention, it is seen that a mixing apparatus is provided for uniformly and gently mixing one or more fluid suspensions, such as blood cell suspensions, in individual containers with means being provided to continually provide a gentle rocking motion to the fluids being mixed. Indicator signals are readily visible by an operator to indicate which of the fluid samples are undergoing mixing for predetermined minimum mixing periods, and which samples have completed their predetermined minimum mixing periods and are ready for removal from the mixing apparatus. With the mixing apparatus 10, random loading of the support platform 40 may be effected while insuring that each of the sample tubes undergoes a minimum mixing time. In this manner, uniform mixing is achieved without distorting, breaking or foaming the blood cell suspensions with the result that more uniform test results between various fluid samples is achieved.

While a preferred embodiment of the present invention has been illustrated and described, it will be understood to those skilled in the art that changes and modifications may be made therein without departing from the invention on its broader aspects.

Various features of the invention are defined in the following claims.

What is claimed is:

1. Mixing apparatus comprising, in combination, base means, a support platform pivotally mounted on said base means for rocking movement about a pivot axis, said support platform defining at least one discrete trough thereon adapted to receive a fluid sample container in supporting relation therein, a drive motor supported by said base means, means interconnecting said drive motor to said support platform so as to effect substantially uniform rocking movement of said platform about said pivot axis when said drive motor is energized, and control means including discrete first signal means operatively associated with each trough and adapted to be energized to provide a signal indicating the presence of a fluid sample container within the corresponding trough, said control means including timer means operatively associated with each of said troughs and operative to maintain said first signal means energized for a predetermined time period after detection of a fluid sample container within the associated trough, said control circuit means further including discrete second signal means operatively associated with each trough and responsive to the corresponding timer means to provide a signal indicating the expiration of a predetermined minimum time period so as to indicate that the corresponding sample container is ready to be removed from said platform.

2. Mixing apparatus as defined in claim 1 wherein said support platform defines a plurality of substantially parallel troughs, said control means including discrete first signal means operatively associated with each of said troughs and adapted to provide a visual indication of the presence of a fluid sample container in each of said troughs.

3. Mixing apparatus as defined in claim 1 wherein said support platform defines a plurality of discrete troughs thereon each of which is adapted to receive a tubular fluid sample container therein such that the longitudinal axes of the containers lie in planes substantially normal and transverse to said pivot axis, said control means including discrete first signal means operatively associated with each of said troughs and adapted to provide a signal indicating the presence of a fluid sample container within the corresponding trough.

4. Mixing apparatus as defined in claim 3 wherein said control means includes second discrete signal means operatively associated with each of said troughs and adapted to provide a visual indication that a predetermined time period has expired after a fluid sample container has been placed within the corresponding troughs.

5. Mixing apparatus as defined in claim 1 wherein said means interconnecting said drive motor to said support platform includes a crank shaft connected to the motor drive shaft, a lever arm fixed to said support platform, and a connecting linkage interconnecting said crank shaft to said lever arm such that rotation of said drive shaft effects cyclical rocking movement of said platform about said pivot axis.

6. Mixing apparatus as defined in claim 1 wherein said at least one trough has a substantially V-shaped transverse configuration defining a pair of angularly inclined support surfaces, said first signal means including a capacitance collector surface disposed on each of said angularly inclined support surfaces and connected in circuit so that a fluid sample container having a surface capacitance charge is operative to energize said first signal means when said container is placed within said trough in contacting relation with said collector surfaces.

7. Mixing apparatus as defined in claim 6 wherein said support platform is made of a dielectric material.

8. Mixing apparatus as defined in claim 5 wherein said drive motor comprises a constant speed motor.

9. Mixing apparatus as defined in claim 1 wherein said control means is adapted to deenergize said first signal means after the expiration of a predetermined minimum time period.

10. Mixing apparatus as defined in claim 9 wherein said control means comprises a control circuit.

11. Mixing apparatus as defined in claim 9 wherein said first and second signal means corresponding to each trough comprise indicator lights of different color.

12. A method for uniformly mixing blood cell suspensions, comprising the steps of:

(a) introducing a quantity of a sample blood cell suspension into a sample container adapted to establish a surface capacitance charge in the presence of the blood cell suspension within said container, (b) placing the sample container on a support platform having means thereon adapted to detect the presence of the container, (c) establishing a first signal indicating the presence of the sample container on the platform, (d) rocking the support platform about a pivot axis in a uniform cyclical rocking movement for a predetermined minimum time period, and (e) establishing a second signal responsive to rocking of said sample container for said predetermined minimum time period whereby to signal that the container may be removed from said support platform.

13. The method as defined in claim 10 wherein said first and second signals are established as visual signal.

* * * * *